United States Patent [19]

Feniou et al.

[11] Patent Number: 4,760,139

[45] Date of Patent: Jul. 26, 1988

[54] METHOD OF PREPARING D-RIBOSE

[75] Inventors: Claude Feniou; Micheline Grignon, both of Pessac; Brigitte Lacourt, Talence; Henri Pontagnier, Pessac; Bernadette Rezzonico, Villenave D'Ornon, all of France

[73] Assignee: Laboratoires Sarget, Cedex, France

[21] Appl. No.: 909,911

[22] Filed: Sep. 22, 1986

[30] Foreign Application Priority Data

Sep. 20, 1985 [FR] France ................... 85 14098

[51] Int. Cl.[4] .................. C07H 1/00; C07H 3/02; C07H 15/04
[52] U.S. Cl. .................. 536/124; 536/18.5; 536/4.1
[58] Field of Search ............ 536/124, 18.5, 4.1

[56] References Cited

U.S. PATENT DOCUMENTS 3,304,298  2/1967  Iwai et al. .................. 536/124 X

FOREIGN PATENT DOCUMENTS 0020172  5/1974  Japan .................. 536/124
0024893  6/1974  Japan .................. 536/124

Primary Examiner—Nicky Chan
Assistant Examiner—Wendy B. Davis
Attorney, Agent, or Firm—Oblon, Fisher, Spivak, McClelland & Maier

[57] ABSTRACT

The present invention relates to a novel method of preparing D-ribose.

In this method, a 1,5-di-O-alkyl derivative of D-xylofuranose is prepared; the hydroxyl groups in positions 2 and 3 are each substituted by a group which is preferably mesyl ($CH_3SO_2$) or methyldithiocarbonyl, $CH_3SC(=S)$; the 2,3-unsaturated derivative is prepared; and D-ribose is finally obtained by cis-hydoxylation of the carbon-carbon double bond, followed by acid hydrolysis of the resulting 1,5-O-dialkyl derivative.

4 Claims, No Drawings

METHOD OF PREPARING D-RIBOSE

BACKGROUND OF THE INVENTION

1. Field of the Invention:

The present invention relates to a novel method of preparing D-ribose.

2. Discussion of the Background:

D-ribose is a monosaccharide present in nature in ribonucleic acids (RNAs) and useful in the preparation of certain medicines, e.g. riboflavin (vitamin B2), adenosine, adenosine monophosphate (AMP), ribavirin, and, in general, a number of virostatic and anticancer agents.

D-ribose is generally manufactured from RNAs of microorganisms. It may also be synthesized from D-erythrose, glutamic acid, or D-ribonic acid (see Merck Index, 10th Ed., 1983, page 8106). However, none of these methods are industrially feasible, because of the difficulty of the synthetic schemes and/or the high price of the raw materials required.

There remains a need for a process for manufacturing D-ribose on an industrial scale using readily available and relatively inexpensive raw materials.

SUMMARY OF THE INVENTION

Accordingly, one object of this invention is to provide a novel method of synthesizing D-ribose from readily available D-xylose.

A further object of this invention is to provide a synthesis of D-ribose by a process suitable for industrial synthetic schemes.

These objects and other objects of the invention which will become apparent from the following specification have been achieved by the present process in which D-ribose is synthesized from D-xylose. The D-xylose is first converted to a 1,5-di-O-alkyl-D-xylofuranose. The hydroxyl groups in the 2 and 3-positions of the dialkyl derivative are then substituted by mesyl or methyldithiocarbonyl groups. The resulting compound is then converted to the 2,3-unsaturated derivative and D-ribose is obtained after cis-hydroxylation and acid hydrolysis.

DETAILED DESCRIPTION OF THE PREFERRED EMBODIMENTS

D-ribose can be synthesized from D-xylose, a monosaccharide which is widely distributed in the vegetable kingdom in the form of xylans.

In a first stage of the method of the present invention, a 1,5-di-O-alkyl derivative of D-xylofuranose, preferably 5-O-trityl-1-O-methyl-D-xylofuranoside, is prepared. The D-xylose is first methylated in the presence of anhydrous methanol and HCl to produce the methyl D-xylofuranoside. The hydroxyl group at the 5-position of the xylofuranoside is then alkylated. The preferred alkyl group is the trityl group (triphenylmethyl group). This alkylation can be accomplished in a suitable solvent such as, for example, anhydrous pyridine.

In the second stage, the hydroxyl groups in positions 2 and 3 are each substituted by a group which is preferably mesyl ($CH_3SO_2$) or methyldithiocarbonyl, $CH_3SC(=S)$. Mesyl substitution can be accomplished by reacting the trityl methyl D-xylofuranoside with mesyl chloride in the presence of anhydrous pyridine. The corresponding methyldithiocarbonyl derivative can be prepared by reacting the trityl methyl D-xylofuranoside with carbon disulfide, sodium hydroxide, iodomethane and tetrabutylyammonium bisulfate in the presence of a dichloromethane solvent.

The 2,3-didesoxy derivative is then prepared from the mesyl derivative by heating the mesyl derivative with KI in the presence of anhydrous DMF. If the methyldithiocarbonyl derivative is used, the didesoxy derivative is formed by heating the methyldithiocarbonyl derivative with $Bu_3SnH$ in the presence of a solvent.

D-ribose is finally obtained by cis-hydroxylation of the carbon-carbon double bond, followed by acid hydrolysis of the 1,5-O-dialkyl derivative. The cis-hydroxylation may be accomplished using cold potassium permanganate and an acetone/water solvent system. The resulting 5-O-alkyl-1-O-methyl-ribofuranoside is then reacted with aqueous sulfuric acid to affect hydrolysis and produce the desired D-ribose. These reactions can be carried out with mixtures of the alpha and beta isomers, or with one of the purified anomers (alpha or beta).

Other features of the invention will become apparent in the course of the following descriptions of exemplary embodiments which are given for illustration of the invention and are not intended to be limiting thereof.

EXAMPLES

Example 1

Synthesis of 1-O-methyl-D-xylofuranoside

To a stirred suspension of 11 g pulverized D-xylose in 200 ml anhydrous methanol there was added 50 ml methanol containing 1 g gaseous HCl. The stirring was continued for 5 hrs. (The solution became clear after 2 hr.) The solution was then neutralized by adding 2.8 g triethylamine with stirring for 0.5 hr. and the solvents were removed by evaporation under reduced pressure. The very small amount of residual D-xylose could be removed by filtration on a silica column (eluent chloroform and 100% ethanol, 8.5:1.5, vol:vol). The Rf of 1-O-methyl-D-xylofuranoside in this solvent system was 0.45 by thin layer chromatography (tlc). The product was used without further purification after the reaction. Yield 95%.

Synthesis of 5-O-trityl-1-O-methyl-D-xylofuranoside

To a solution of 10 g of the compound prepared above in 40 ml anhydrous pyridine there was added 17 g trityl chloride, in small portions. The medium was cooled to 0° C. The introduction of trityl chloride was accompanied by a brown coloration of the medium, and after ½ hr of stirring a white precipitate formed. The solution was allowed to return to room temperature, and was held for 48 hours under an inert atmosphere. The chloride formed was filtered out over Celite and the pyridine was removed by evaporation under reduced pressure. The organic phase was then twice coevaporated with toluene. The 5-O-trityl-1-O-methyl-D-xylofuranoside was purified by chromatography on a silica column (eluent hexane and ethanol, 9:1, vol:vol). The Rf of the product in this solvent system was 0.20 by tlc. The product was obtained in the form of a white foamy material, with a yield of 85%.

Synthesis of 5-O-trityl-2,3-di-O-mesyl-1-O-methyl-D-xylofuranoside

To a solution of 3 g of the compound prepared above in 15 ml anhydrous pyridine there was added dropwise 2.5 ml mesyl chloride. During the entire period of the addition the reaction mixture was held at 0° C. The mixture was then allowed to return to ambient temperature under an inert atmosphere. After 15 minutes the chloride began to precipitate. After being set aside for 20 hour, the solution had a black color. The reaction mixture was poured into 40 ml of a water and ice mixture and was extracted twice with chloroform. The organic phases were recombined, dried, and evaporated under reduced pressure, and were then twice co-evaporated with 50 ml toluene. The desired product was obtained in the form of an orange foamy material, with a yield of 91%. The product was purified by chromatography on a silica column (eluent hexane and ethanol, 95:5, vol:vol).

It is possible to isolate the two anomers. The beta anomer is soluble in hot cyclohexane, and precipitates. The alpha anomer is then obtained by evaporation of the mother liquors.

Synthesis of
5-O-trityl-1-O-methyl-2,3-didesoxy-D-xylo-2-pentenofuranoside 1 g Zn/Cu couple and 2.5 g KI in solution in 10 ml anhydrous DMF were placed in a flask. The mixture was degassed by passing argon through it. 1.7 g of the product prepared above, in the form of a 50-50 mixture of the alpha and beta anomers, was added dropwise with stirring to this suspension. The mixture was heated for 4 hours under reflux. The hot solution was then poured into 40 ml of a 50-50 mixture of ice and water, and 30 ml chloroform was added. Stirring was continued for 15 minutes. The mixture was then filtered through Celite to remove the metal salts, and the Celite cake was washed twice with a 50:50 mixture by weight of water:chloroform. The chloroform phases were recombined, washed with a saturated sodium thiosulfate solution and then with water, were dried, and were evaporated under reduced pressure. Nearly all the DMF was eliminated in the aqueous phase, but traces remained in the organic phase which required a vacuum pump for removal. The desired product was recovered by chromatography on a silica column (eluent hexane:ethanol, 95:5, vol:vol), in the form of a slightly yellowish oil, with a yield of 70%.

The product was a mixture containing 80% beta anomer and 20% alpha monomer NMR proton spectral characteristics are given below for each of the two anomers, in CDCL$_3$ with tetramethylsilane (TMS) as the internal standard. The first value of the chemical shift corresponds to the beta anomer, and the second value, in parentheses, to the alpha anomer.

3.07–3.3 ppm (3.2–3.3 ppm), 2 multiplets, CH$_2$; 3.42 ppm (3.38 ppm), 1 singlet, OCH$_3$; 4.86 ppm (4.86 ppm), 1 multiplet, J$_{34}$=2 Hz, J$_{24}$=1.25 Hz, C4-H; 5.74 ppm (5.74 ppm), 1 doublet, J$_{12}$=1.25 Hz, C1-H; 5.8 ppm (5.84 ppm), 1 multplet, J$_{13}$=1 Hz, C3-H; 7.164 7.52 ppm (7.16–7.52 ppm), 2 multiplets (C$_6$H$_5$)$_3$C.

Synthesis of
5-O-trityl-1-O-methyl-beta-D-ribofuranoside

To a solution of 1.15 g of the beta anomer of the unsaturated compound obtained above, in 12 ml acetone and 6 ml water and cooled in an ice and salt bath to −10° C., there was added dropwise 0.7 g potassium permanganate which had been previously pulverized and dissolved in a mixture of acetone (12 ml) and water (4 ml). The temperature was held constant during the addition, approximately 2 hours. Then the reaction mixture was allowed to return to ambient temperature.

A change in color was observed from rose to maroon. After vigorous stirring overnight, the reaction mixture was filtered. The salts of manganese which were retained on the filter were washed with dichloromethane, and the filtrate was extracted with dichloromethane. The organic phases were recombined, washed with water, and dried. The solvent was removed by evaporation under reduced pressure. The raw product thus obtained had a slightly yellowish color, and was obtained with a yield of 74%. It was purified on a silica column (eluent chloroform and ethanol, 9:1, vol:vol). The Rf of the product with this solvent system was 0.53 by tlc. A slightly yellowish fraction was isolated, corresponding to the beta-riboside. Its NMR spectrum was identical to that of a comparison sample prepared from D-ribose by reaction with methanol followed by trityl chloride (yield of the comparison sample—52%).

The NMR proton spectrum at 200 MHz was determined for the product in CDCl$_3$, with TMS as the internal standard, as follows: 3.2 ppm, doublet, J$_{45}$=5.30 Hz, CH$_2$; 3.25 ppm, singlet, OCH$_3$; 3.94 ppm, doublet, J$_{23}$=4.75 Hz, C2-H; 4.01 ppm, multiplet, C4-H; 4.17 ppm, doublet, split, J$_{34}$=7.15 Hz, C3-H; 4.79 ppm, singlet, C1-H; 7.15–7.45 ppm, 2 multiplets, (C$_6$H$_5$)$_3$C. With the continuous wave spectrum at 60 MHz, in CDCl$_3$ with TMS as the internal standard, a major broadening occurs at 3 ppm which corresponds to 2 OH.

Synthesis of D-ribose 1.g 5-O-trityl-1-O-methyl-ribofuranoside was mixed with 10 g of 1N aqueous sulfuric acid, in a flask fitted with reflux condenser. The mixture was heated to 100° C., under stirring. The sugar liberated was dissolved in the water, while trityl alcohol precipitated out. After an hour, the mixture was cooled to room temperature and was filtered. The filtrate was neutralized with aqueous sodium hydroxide, and was evaporated to dryness. The residue was recrystallized in 15 cc absolute ethanol. The insoluble sodium sulfate formed in the neutralization was removed by filtration. In this way, the D-ribose was isolated in the form of an oil. The resulting raw product was purified by passage through a silica column (eluent chloroform:ethanol, 80:20, vol:vol). The physicochemical characteristics of the purified product were as follows: m.p. 87°–88° C.; alpha(D) optical rotation at 21° C.=−26 for c=3 in water, read after 15 min; Rf=0.65 for alumina tlc with the eluent isopropanol:water (80:20).

Example 2

Synthesis of
5-O-trityl-2,3-di-O-methyldithiocarbonyl-1-O-methyl-D-xylofuranoside To a solution of 4.06 g 5-O-trityl-1-O-methyl-D-xylofuranoside prepared according to Example 1, in 70 ml dichloromethane, there was added successively 6.8 g tetrabutylammonium bisulfate (a phase transfer agent), 70 ml 50% sodium hydroxide, 2 ml carbon disulfide, and 3.2 g iodomethane. The mixture thickened and acquired an orange color. Stirring was continued for 30 min, and the reaction was monitored by tlc (eluent hexane:ethanol, 9:1, vol:vol). 200 g ice was added, and the mixture was then extracted with 200 ml ether. After decantation, the aqueous phase was twice extracted with 100 ml ether. The organic phases were then washed with water, dried, and evaporated under reduced pressure. The raw product (yield 95%) had the appearance of an oil. It was purified by chromatography on silica gel (eluent hexane:ethanol, 9:1, vol:vol) with a yield of 94%.

The anomers can be separated by recrystallization, with the alpha anomer being obtained in a cyclohexane:ethanol mixture (80:20), and the beta anomer in the mother liquors.

Synthesis of 5-O-trityl-1-O-methyl-2,3-didesoxy-D-xylo-2-pentenofuranoside

A solution of 3.36 g Bu$_3$SnH in 30 ml toluene was heated in a flask. A solution of 0.85 g of the thioester prepared above, in 30 ml toluene, was added dropwise with stirring. The mixture was then degassed by argon bubbling and the reaction was monitored by tlc. Reflux was continued for 24 hours, after which it was noted that the original yellowish color had disappeared. The toluene was removed by evaporation. The residue was added to 35 ml ether, and this mixture was stirred vigorously with a saturated solution of KF until a white precipitate formed. The washing with KF was repeated twice. The organic phases were then washed with water, followed by drying, and evaporation under reduced pressure. After purification by chromatography on a silica column (eluent hexane:ether, with the ether employed in an increasing proportion which ultimately reached 30 vol.%), a yellowish oil was obtained. The yield was 50% when the starting material was 50-50 mixture of the alpha and beta anomers; 80% when the starting material was pure beta anomer; and 23% when pure alpha anomer.

D-ribose was then prepared from this product by the method described in Example 1.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of synthesizing D-ribose, comprising the steps of:
   preparing a 1,5-di-O-alkyl-D-xylofuranoside from D-xylose;
   substituting a member selected from the group consisting of a mesyl group and a methyldithiocarbonyl group for each of the protons of the hydroxyl groups at C2 and C3;
   forming the 1,5-di-O-alkyl-2,3-didesoxy-D-2-xylopentenofuranoside;
   cis-hydroxylating said xylopentenofuranoside; and
   acid hydrolyzing the product of said cis-hydroxylating step.

2. The method of claim 1, wherein a mesyl group is substituted for each of said protons during said substituting step.

3. The method of claim 1, wherein a methyldithiocarbonyl is substituted for each of said protons in said substituting step.

4. The method of claim 1, further comprising:
   isolating the beta isomer of said xylopentenofuranoside before performing said cis-hydroxylating step.

* * * * *